US00PP23483P2

(12) United States Plant Patent
Hurd

(10) Patent No.: US PP23,483 P2
(45) Date of Patent: Mar. 19, 2013

(54) ***DIANTHUS* PLANT NAMED 'FIRE AND ICE'**

(50) Latin Name: ***Dianthus* hybrid**
Varietal Denomination: Fire and Ice

(75) Inventor: Kevin A. Hurd, Chicago, IL (US)

(73) Assignee: Walters Gardens, Inc., Zeeland, MI (US)

( * ) Notice: Subject to any disclaimer, the term of this patent is extended or adjusted under 35 U.S.C. 154(b) by 75 days.

(21) Appl. No.: 13/135,645

(22) Filed: Jul. 12, 2011

(51) Int. Cl.
*A01H 5/00* (2006.01)

(52) U.S. Cl. ..... Plt./272; Plt./282

(58) Field of Classification Search ..... Plt./282, Plt./281, 277, 276, 272
See application file for complete search history.

*Primary Examiner* — Kent L Bell

(57) ABSTRACT

A new and unique cultivar of perennial plant Carnation or Pinks, *Dianthus* plant named 'Fire and Ice' with long-blooming, fragrant, single flowers, with overlapping petals of deep raspberry with irregular fine flecks of pink and up to two larger pink spots. The petals have a margin of light pink becoming nearly white. *Dianthus* 'Fire and Ice' is tolerant of high temperatures and resists center die-out.

1 Drawing Sheet

Botanical denomination: *Dianthus* hybrid.
Cultivar designation: 'Fire and Ice'.

BACKGROUND OF THE INVENTION

The present invention relates to the new and distinct cultivar of *Dianthus* or Pinks from the genus *Dianthus* and given the cultivar name 'Fire and Ice' previously known internally by the breeder code DIA070720. The new plant was the result of an intentional cross in May of 2007 by Kevin A. Hurd between *Dianthus* 'Strawberry Sorbet' U.S. Plant Pat. No. 18,338 as the female or seed parent and 'Cranberry Ice' U.S. Plant Pat. No. 18,342) as the male or pollen parent. The new hybrid was first isolated from trials at a nursery in Zeeland, Mich. during the summer of 2008. *Dianthus* 'Fire and Ice' has been asexually propagated at the same nursery in Zeeland, Mich. using traditional shoot tip cutting procedures and found to reproduce plants that are identical and exhibit all the characteristics of the original plant.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant. The new plant is distinct from its parents and all other *Dianthus* known to the applicant in the following combined traits:

1. Flat, single, overlapping petals of deep raspberry with irregular fine flecks of pink and up to two larger pink spots,
2. Petals having a margin of light pink becoming nearly white,
3. High heat tolerance with no vernalization required for flower production,
4. Floriferous, vigorous and excellent habit, and
5. Compact, fine-textured, blue-green foliage.

Cultivar Comparison Table

| Cultivar | Flower color | Flower pattern | Flower diameter | Color Petal margin |
|---|---|---|---|---|
| 'Cranberry Ice' U.S. Plant Pat. No. 18,342 | pink | dark wine edge and rim | 3.3 cm | dark wine margin |
| 'Devon Siskin' U.S. Plant Pat. No. 14,377 (Raspberry Swirl) | red purple | magenta edge with burgundy base and light pink eye | 4.0 cm | magenta margin with white edge |
| 'Devon Xera' U.S. Plant Pat. No. 14,895 (Fire Star) | crimson | crimson eye | 3.0 cm | self |
| 'Feuerhexe'(not patented) | fuchsia pink | solid | 4.0 cm | self |
| 'Fire and Ice' | raspberry | pink flecking and light pink to nearly white petal margins | 3.5 cm | light pink becoming nearly white |
| Red Dwarf' U.S. Plant Pat. No. 14,437 (Eastern Star) | red | crimson eye | 3.5 cm | self |
| 'Ruby Sparkles' (co-pending) | magenta red | round deep ruby eye | 4.5 cm | deep rose pink |
| 'Spangled Star' U.S. Plant Pat. No. 13,029 | red | pale pink blotch and eye | 4.0 cm | pale pink |
| 'Strawberry Sorbet' U.S. Plant Pat. No. 18,338 | bright red | light pink | 4.0 cm | light pink to white |
| 'Very Cherry' (co-pending) | black-red | burgundy eye and streaks | 3.5 cm | bright red |
| 'Sangria Splash' U.S. Plant Pat. No. 21,781 | fuchsia pink | crimson ring with pink splashing and center | 3.0 cm | crimson with pink splashing |

| Cultivar | Petal edge | Petal # | Plant height In flower |
|---|---|---|---|
| 'Cranberry Ice' U.S. Plant Pat. No. 18,342 | moderately serrated | 5 | 20 to 25 cm |

-continued

| Cultivar Comparison Table | | | |
|---|---|---|---|
| 'Devon Siskin' U.S. Plant Pat. No. 14,377 (Raspberry Swirl) | very fine serration | 5 | 10 cm |
| 'Devon Xera' U.S. Plant Pat. No. 14,895 (Fire Star) | coarsely serrated | 5 | 15 to 20 cm |
| 'Feuerhexe'(not patented) | deeply serrated | 5 | 10 to 12 cm |
| 'Fire and Ice' | Very fine serrated | 5 | 20 to 25 cm |
| Red Dwarf' U.S. Plant Pat. No. 14,437 (Eastern Star) | rounded serration | 5 | 20 to 25 cm |
| 'Ruby Sparkles' (co-pending) | coarsely serrated | 5 | 15 to 20 cm |
| 'Spangled Star' U.S. Plant Pat. No. 13,029 | minutely serrated | 5 | 17 to 22 cm |
| 'Strawberry Sorbet' U.S. Plant Pat. No. 18,338 | moderately serrated | 5 | 15 to 20 cm |
| 'Very Cherry' (co-pending) | finely serrated | 5 | 25 to 30 cm |
| 'Sangria Splash' U.S. Plant Pat. No. 21,781 | variably serrated | 5 | 30 cm |

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

FIG. 1 shows a close-up of the flower.

DETAILED DESCRIPTION OF THE PLANT

The following detailed description of the new plant is based on observations of one-year old plants in greenhouse-grown container at a nursery in Zeeland, Mich. with light shade, supplemental watering, light additions of fertilizer and free of other plant growth regulators. All color usage is in accordance with The 2001 edition of The Royal Horticultural Colour Chart except where common dictionary terms are used.

Botanical classification: *Dianthus* hybrid.

Parentage: 'Strawberry Sorbet' U.S. Plant Pat. No. 18,338 as the female or seed parent and 'Cranberry Ice' U.S. Plant Pat. No. 18,342) as the male or pollen parent.

Plant description:

*Habit*.—Cespitose, herbaceous, evergreen perennial; stems proximally branched, erect; height of foliage about 9.0 cm and 30.0 cm across; height in flower is about 25.0 cm; Root system; fine, fibrous.

Foliage:

*Leaf type*.—Simple, linear, opposite, decussate, sessile, glabrous, glaucous on adaxial and abaxial; margin entire, acute apex; base decurrent, adpressed along stem and somewhat perfoliate; no fragrance detected.

*Leaf dimensions*.—About 10.0 cm long and 5.0 mm wide.

*Leaf color*.—More green than RHS 122B and more blue than RHS 133C on adaxial and abaxial sides.

*Venation*.—Finely reticulate, coloration same as that of leaf top and bottom.

*Stems*.—Erect to slightly arching, terete, glabrous, glaucous, proximally branching at 2 to 3 nodes.

*Stem size*.—About 25 cm long and 3 mm wide at base.

*Stem color*.—Nearest RHS 122B.

*Branching*.—Numerous from lower leaf axils; about 200 per plant.

*Nodes*.—3 mm across, RHS N122C.

*Internodes*.—6.5 cm apart depending on growing temperature, shorter in cooler conditions.

Inflorescence:

*Type*.—Terminal, cymose, erect, symmetrical.

*Dimension*.—About 3.5 cm across and extending about 7.0 mm above calyx.

*Flowers per stem*.—3 to 4.

*Pedicel*.—Glaucous, glabrous, terete.

*Pedicel size*.—Usually 2.0 to 2.5 cm long and 2 mm diameter.

*Pedicel color*.—Nearest RHS 122A.

Flowers:

*Type*.—Salverform, single, symmetrical.

*Flower bud shape*.—Rhomboid to terete.

*Flower bud size one day prior to opening*.—About 2.2 cm long and 0.5 cm wide.

*Flower bud color*.—Glaucous, nearest RHS N138B; tinted with anthocyanin nearest RHS N77D.

*Flower period*.—Beginning late May and flowering until frost in the fall with a short 2 week rest after the initial period of four weeks.

*Flower fragrance*.—Light, sweet spicy, clove-like.

*Flower lasting quality*.—About five days on or off the plant.

*Petals*.—Five, consisting of a rounded blade or limb and a claw; blade and claw combined are obovate; apex and margin finely serrulate with dentations 0.5 mm deep, bearded with minute hairs mostly on the center of the adaxial surface; outer petal margin of about 1.0 mm wide; bent outwardly about 6.0 mm above the calyx to nearly a ninety degree angle forming the limb; claw tapering to truncate base.

*Petal color*.—Petal limb base adaxial side between RHS N79B and RHS N79C with numerous fine spots of less than 0.5 mm diameter of RHS 73A and up to two larger spots about 3.0 mm across nearest RHS 73A, margin of lighter than RHS N74D becoming near white, much lighter than RHS 69D and RHS N155C; abaxial side limb between RHS 76C and RHS 76D; adaxial side of petal limb lightens to between RHS 73B and RHS 73C; claw consistent RHS 145B on both surfaces for the 1.5 cm portion within the calyx and lighter than RHS 69D on the abaxial surface above the calyx and RHS 73A above the calyx on the adaxial surface.

*Petal dimension*.—About 3.2 cm long extended including claw and limb; petal limb about 1.5 cm long and 1.4 cm wide; claws about 1.8 cm long and 1.0 mm wide at base and 3.0 mm wide below limb.

*Calyx*.—Glabrous, glaucous; consisting of five sepals with acute apex and fused base making up a five-toothed corolla tube fused in proximal 1.4 cm; about 2.0 cm long and 0.6 cm in diameter; nearest RHS 138B in adaxial surface and nearest RHS 137B on abaxial surface; individual sepals with entire margins.

*Peduncle*.—Glabrous, glaucous, terete, 22 cm long and 2 mm diameter at base; nearest RHS N138D.

*Bracts*.—Two, opposite, glaucous, entire, broadly obtuse with rounded apex, about 5.0 mm long and 3.5 mm wide; between RHS 141A and RHS 141B in the center of both adaxial and abaxial surfaces, nearest RHS 142C at base and margins.

*Bracteoles*.—Two, opposite and at 90 degrees offset from bracts, oblanceolate, sharply acute apex, bases joined at stem; about 4.0 mm long and 3.0 mm wide; glaucous, entire; RHS 141A at apex and center, nearest RHS 142C at base and margins.

*Androecium*.—Usually 10 stamens. Filaments: variable in length from 1.6 cm to 2.5 cm long, less than 1 mm diameter, dorsifixed; very pale red-purple much lighter than RHS 72D. Anther: elliptic-oblong, about 3.0 mm long and1.0 mm wide, nearest RHS 186D; pollen; less than 0.1 mm across; color nearest RHS 158C.

*Gynoecium*.—Style: split in two above ovary. Pistil: about 2.5 cm long and about 1.0 mm diameter; much lighter than RHS 63D. Stigma: about 1.0 cm long and 1.0 mm wide; curled around nearly 270 degrees at maturity; much lighter than RHS 63D. Ovary: superior to androecium and inferior to gynoecium, spindle-shaped; about 8.0 mm long and 3.0 mm wide; RHS 145A at distal end and between RHS 145 D and RHS 145 C at proximal end.

Seed: Only few have been observed; blackish brown darker than RHS 200A, shield-shaped, dorsiventrally compressed, about 3.0 mm across and 0.5 mm thick.

Capsule: Ovoid to cylindrical, opening by 4 teeth, about 2 cm long and 8.5 mm diameter, between RHS 164B and RHS 164A when dried.

Disease resistance: The new plant is resistance to center die out from fungus or high temperatures. The plant grows best with adequate moisture and well-drained soil, but is able to tolerate high temperatures and some drought once established. Hardiness at least from USDA zone 4 through zone 9.

I claim:

1. A new and distinct *Dianthus* plant named 'Fire and Ice' essentially as herein described and illustrated and suitable as a garden ornamental, potted plant and for cut flower arrangements.

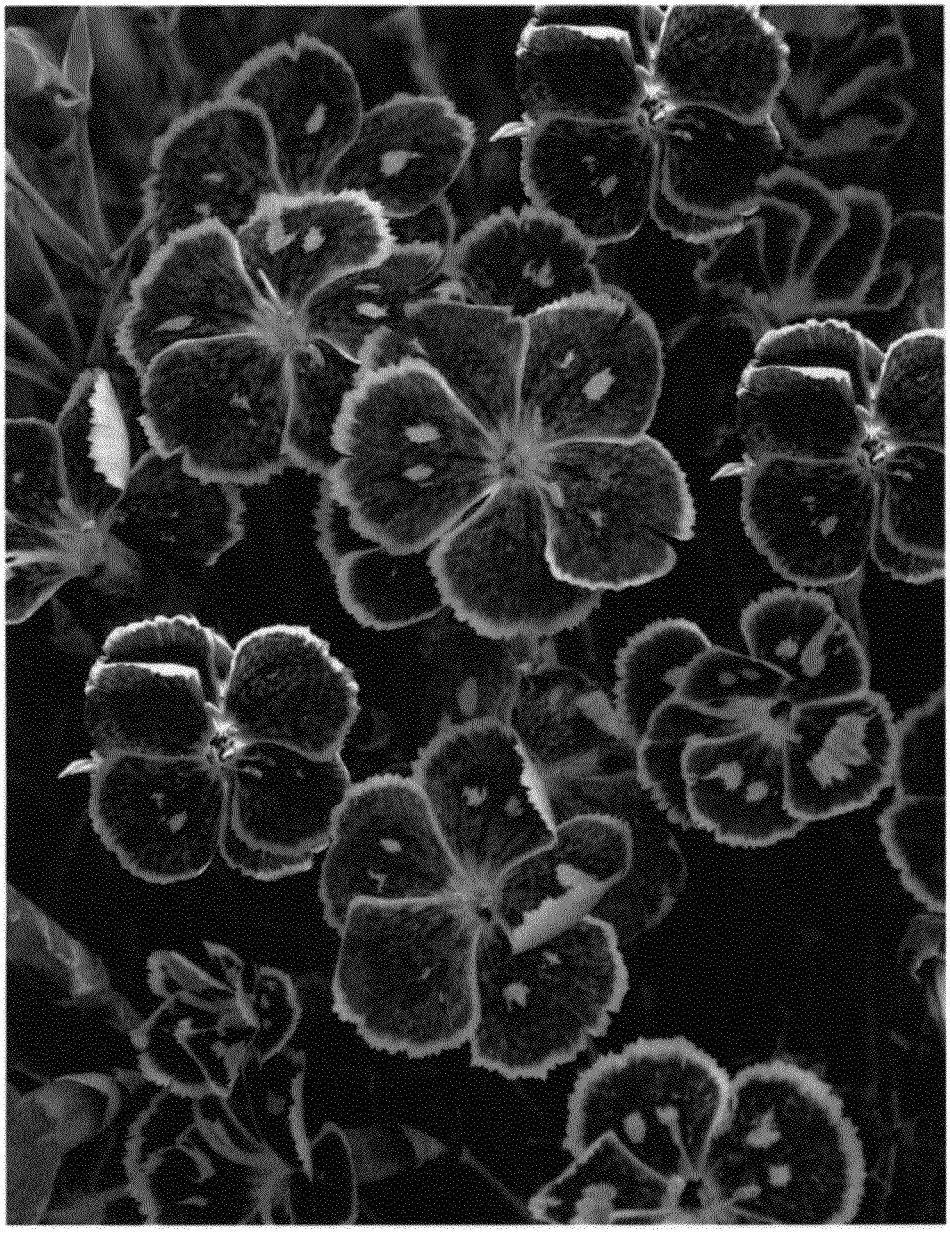

* * * * *